(12) United States Patent
Baldauf et al.

(10) Patent No.: US 8,347,466 B2
(45) Date of Patent: Jan. 8, 2013

(54) LOOP TAPE FOR HOOK-AND-LOOP FASTENER

(75) Inventors: Georg Baldauf, Laer (DE); Dieter Homoelle, Ochtrup (DE)

(73) Assignee: Mondi Gronau GmbH, Gronau (DE)

( * ) Notice: Subject to any disclaimer, the term of this patent is extended or adjusted under 35 U.S.C. 154(b) by 465 days.

(21) Appl. No.: 12/627,093

(22) Filed: Nov. 30, 2009

(65) Prior Publication Data

US 2010/0132412 A1     Jun. 3, 2010

(30) Foreign Application Priority Data

Nov. 28, 2008   (DE) .......................... 10 2008 059 512

(51) Int. Cl.
 *A44B 18/00*    (2006.01)
(52) U.S. Cl. ....................................................... 24/442

(58) Field of Classification Search .................... None
See application file for complete search history.

(56) References Cited

U.S. PATENT DOCUMENTS 6,647,600 B1   11/2003 Joest ............................... 24/442
7,670,663 B2 *  3/2010 Poulakis ....................... 428/100

FOREIGN PATENT DOCUMENTS

DE       102006038377       10/2007

* cited by examiner

*Primary Examiner* — Jack W. Lavinder
(74) *Attorney, Agent, or Firm* — Andrew Wilford

(57) ABSTRACT

A loop element for a hook-and-loop fastener has a substrate layer of a nonwoven having an outer face, a fleece cover layer on the outer face of the substrate layer, and an adhesive layer on the outer face securing the cover layer to the substrate layer. A multiplicity of loops formed of polymer threads are knitted into only the cover layer and project from an outer face thereof.

18 Claims, 1 Drawing Sheet

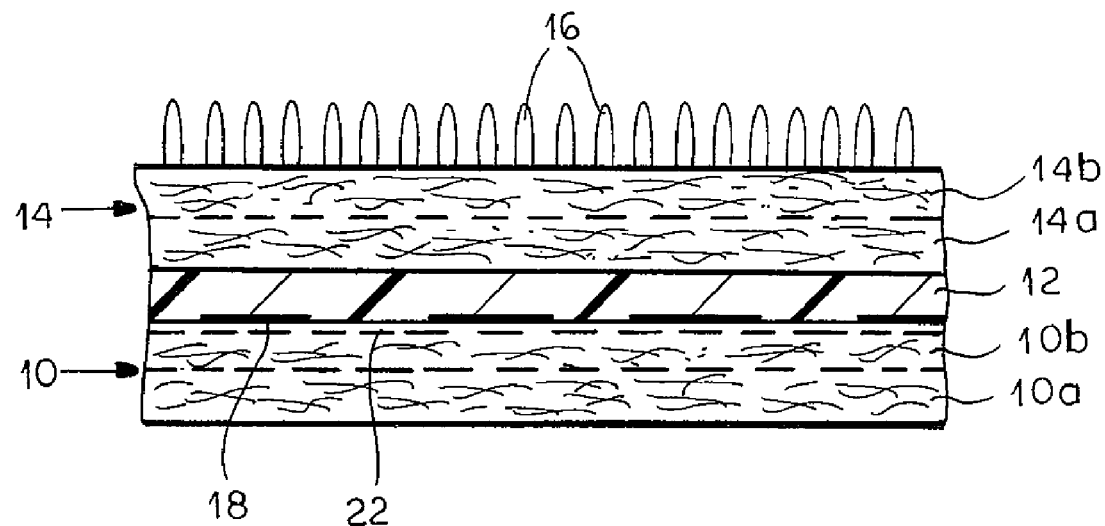
F I G.1
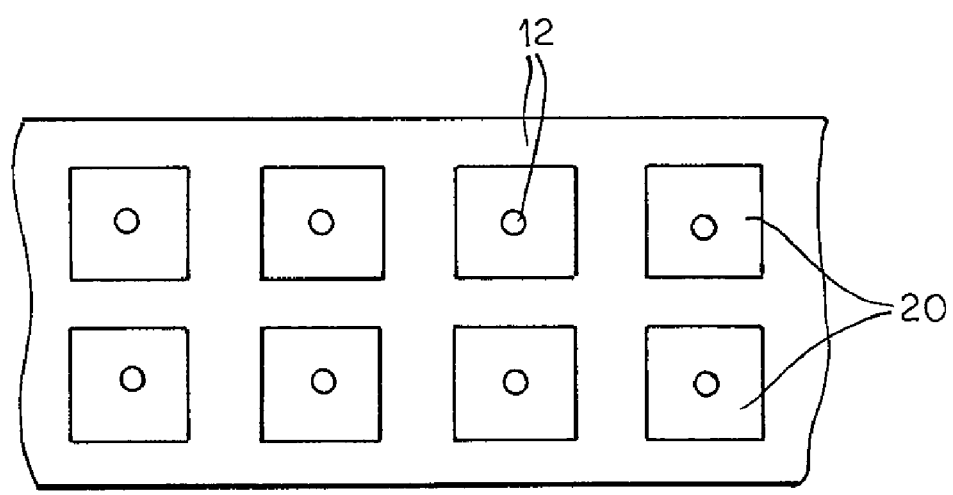
F I G.2

LOOP TAPE FOR HOOK-AND-LOOP FASTENER

FIELD OF THE INVENTION

The present invention relates to a hook-and-loop fastener. More particularly this invention concerns a loop tape or strip for such a fastener.

BACKGROUND OF THE INVENTION

A laminate element, typically a strip or tape, for a hook and loop fastener, particularly for a diaper, has a substrate layer and a textile cover layer laminated onto the substrate layer. The cover layer has free loops for engagement of hook elements of the other fastener half, that is the hook tape or strip. This cover layer typically consists of a nonwoven material and polymer threads knitted into it and forming the loops.

The laminate forms the female part of a hook and loop fastener. When used on diapers, the laminate is applied to the front waistband region of the diaper. A hook tape, which is attached at the side of the diaper and has hooks at its free end, completes the hook-and-loop fastener. Hook-and-loop fasteners can be opened and closed many times without any deterioration of functionality. In contrast to adhesive fasteners, hook-and-loop fasteners are not sensitive to contact with skin creams or powder.

Various demands are made on a laminate for a hook-and-loop fastener on a disposable product, for example baby diapers. The material is supposed to have as low a weight per area unit as possible so that it can be produced inexpensively. In spite of its low weight per area unit, the material must guarantee sufficient hook engagement with hooks of the related hook tape. A sufficient number of freely movable loops is required, whose function is not allowed to be impaired by adhesion of the substrate layer to the textile cover layer. Last but not least, the material is supposed to have an appearance that appeals to the consumer.

A laminate having the characteristics described above is known from U.S. Pat. No. 6,647,600, where a multi-layer nonwoven laminate is provided as the textile cover layer, and where textured polymer threads are knitted into the entire nonwoven laminate to form the loops. In order to achieve a good printing surface and adhesive surface, the cover layer can optionally be laminated onto a film as a substrate layer, onto which film the print or the adhesive layer is then applied. If, according to an alternative embodiment, no substrate layer is provided, there is the disadvantage that the nonwoven laminate must have a comparatively great thickness in order to guarantee sufficient strength. If the nonwoven laminate material with the polymer threads knitted into it is supposed to be used as a substrate layer without a film, the nonwoven laminate can be provided with an adhesive on an outside layer, in order to allow attachment of the laminate, for example on a diaper. In this connection, the opposite side can be provided with an print. It is disadvantageous that the print, which then lies on the outside after attachment by the adhesive, can easily be rubbed off. In particular, undesirable contamination can occur when the laminate is used. Furthermore, because of the loops that project out of the nonwoven laminate on the one hand and the low weight per area unit that is usually aimed at for cost reasons on the other hand, a uniform print is not possible, or only possible with difficulty.

DE 10 2006 028 377 describes a textile laminate material having a substrate layer and a cover layer that are stitched together. The sewing forms loops for the engagement of hook elements on the top of the laminate material and stitches on the underside of the laminate material. The substrate layer and the cover layer can consist of nonwoven materials. Compromises have to be made with regard to the hook-and-loop properties and laminate strength, since in a warp-knitting process with the same sewing threads not only are free loops formed but also the layers are connected with one another.

OBJECTS OF THE INVENTION

It is therefore an object of the present invention to provide an improved loop tape for hook-and-loop fastener.

Another object is the provision of such an improved loop tape for hook-and-loop fastener that overcomes the above-given disadvantages, in particular that has a pleasant feel and high-quality visual properties, and, at the same time, demonstrates good usage properties.

Further according to the invention the laminate should have loops on the top, for use in a hook-and-loop fastener, on which hook elements adhere well, and is supposed to allow a good transfer of force in a hook-and-loop fastener.

Furthermore, the laminate strength of the laminate is supposed to meet high requirements.

SUMMARY OF THE INVENTION

A loop element for a hook-and-loop fastener has according to the invention a substrate layer of a nonwoven having an outer face, a fleece cover layer on the outer face of the substrate layer, and an adhesive layer on the outer face securing the cover layer to the substrate layer. A multiplicity of loops formed of polymer threads are knitted into only the cover layer and project from an outer face thereof.

BRIEF DESCRIPTION OF THE DRAWING

The invention described above and other objects, features, and advantages will become more readily apparent from the following description, reference being made to the accompanying drawing in which:

FIG. 1 is a large-scale section through a loop element according to the invention; and FIG. 2 is a smaller-scale top view of the substrate layer.

SPECIFIC DESCRIPTION

As seen in FIG. 1 a loop laminate according to the invention comprises a base layer 10 formed of a nonwoven, here actually two layers 10a and 10b. The layer 10b is a spunbond and has an outer face secured by an adhesive layer 12 to a cover layer 14 formed of two layers 12a and 12b of fleece. Polymer filaments 16 forming loops are knitted into only the cover layer 14.

The outer (here upper) face of the nonwoven layer 10 is provided with a primer coating 22 as described below and may be corona-discharge or plasma treated. Indicia 18 is printed atop this coating.

FIG. 2 shows that the adhesive 12, which may be applied over the entire confronting surfaces of the layers 10 and 14, may also be applied in a pattern, here a perimeter frame, a grid of crossing strips, and dots in adhesive-free zones 20. The coverage of the adhesive 12 is as described below.

More specifically, the cover layer 14 of the laminate according to the invention is formed from a fleece and polymer threads 16 knitted into it. The fleece forms a planar basic structure. The polymer threads 16 are worked into the fleece, i.e. worked in using a knitting process, with the formation of stitches, and form free loops for engagement into hook elements. By knitting separate polymer threads 16 in, loops having a precisely defined size can be produced in a uniform arrangement, allowing a particularly reliable connection with hooks of a hook element. The substrate layer 10 represents a layer independent of the cover layer 14, which gives the laminate its strength and the stability required for use as a hook-and-loop element. The textile substrate layer 10, on the one hand, and the cover layer 14 with the loops knitted into it, on the other hand, can be produced separately from one another and subsequently connected by adhesive lamination. The laminate according to the invention has an air-permeable structure and is furthermore characterized by a pleasing, soft feel. It gives a very high-quality, textile impression.

According to a preferred embodiment of the present invention, the substrate layer 10 is printed on its inner side that faces the cover layer 14. In this way, the printed indicia 18 is protected by the cover layer 14, in particularly advantageous manner. However, since the cover layer 14 is usually thin and translucent, the printed indicia 18 remains clearly visible. Because of the weight per area unit that is typically provided, printing of the cover layer 14 is not possible or only possible with difficulties, while the substrate layer 10, which is particularly supposed to guarantee sufficient shape stability, can be printed on relatively easily.

For printing the substrate layer 10, a rotary printing method can particularly be provided. The rotary printing method is characterized by its economic efficiency, in spite of comparatively high setup costs for large-volume printing. Thus, very high web speeds and therefore also a high throughput can be implemented with the rotary printing method. The rotary printing method preferably takes place by an intaglio printing technique, where both direct and indirect intaglio printing can be carried out. In the case of direct intaglio printing, the ink is applied to the substrate directly from wells or impressions in the printing cylinder. In indirect intaglio printing, ink from the wells is first applied to an impression cylinder, which is typically made of rubber, and from there to the nonwoven. While more uniform ink application can be achieved with indirect intaglio printing, direct intaglio printing also easily allows the application of large amounts of ink.

According to a preferred embodiment of the invention, the fleece of the cover layer 14 consists of non-curled endless filaments. A spun-bonded fleece, for example, is well suited for introduction of the polymer threads 16 that form the loops, by warp-knitting technology. Since the cover layer 14 is laminated onto a substrate layer 10, within the scope of the invention, a low weight per area unit of the cover layer 14 is generally sufficient. In this connection, it must be guaranteed that when using the laminate together with a hook tape of a hook-and-loop fastener, the loops formed by the polymer threads 16 are not torn out. The strength of the laminate as such, however, can be achieved by a correspondingly stable configuration of the printed substrate layer 10. Basically, however, it can also be provided that the cover layer 14 is formed from at least two fleece layers 14a and 14b into which the polymer threads 16 are knitted. In particular, fleece layers 14a and 14b having different fiber structures can also be combined. In the case of such a multi-layer configuration of the cover layer 14, this makes a significant contribution to the required strength of the entire laminate.

According to the present invention, the substrate layer 10 consists of nonwoven. Nonwoven is understood to mean planar fiber nonwoven materials. The term comprises both staple fiber nonwoven goods and spun-bonded nonwoven materials made from endless filament fibers. Because of its higher tear strength, a spun-bonded nonwoven material or a multi-layer nonwoven material having at least one outer layer made of spun-bonded nonwoven is particularly suitable. A multi-layer nonwoven that has outer layers of spun-bonded nonwoven material (spunbond S) and, between them, at least one layer of melt-blown fibers (melt-blown M) is preferred. These multi-layer nonwoven materials having a layer structure SMS, SMMS, or SMMMS, are usually characterized, as compared with a purely spun-bonded nonwoven material, by a more uniform surface structure and thus better printability. The nonwoven can consist of polyolefin fibers, polyamide fibers, polyester fibers, or fiber mixtures of the materials mentioned. It is practical if the weight per area unit of the nonwoven used as the substrate layer 10 lies in a range between 10 $g/m^2$ and 30 $g/m^2$. The nonwoven material used is preferably a SMS made of polypropylene, in the weight range of 15 $g/m^2$. As described above, for many applications, formation of the cover layer 14 with a single layer, particularly a single layer of spun-bonded fleece, is sufficient. However, if the cover layer 14 itself is is supposed to demonstrate greater strength, the layer structure described with reference to the nonwoven of the substrate layer 10 can also be provided.

The polymer threads 16 knitted into the fleece of the cover layer 14 can be monofilaments or multicomponent filaments. Use of non-textured threads, particularly non-textured multipart filaments, is preferred, since they are inexpensive and easy to process. Furthermore, the loops formed by such a thread, when the laminate is used as part of a hook-and-loop fastener, can easily be connected with related hook elements. In this connection, the invention is based on the recognition that in order to produce a firm connection, the hook elements of a hook-and-loop fastener preferably engage completely through the loops formed by the polymer threads 16. For certain application cases, however, it can also be practical to provide for texturing of the threads.

It is practical if the polymer threads 16 are knitted into the fleece of the cover layer 14 by a stitch-bonding process. The Maliwatt stitch-bonding technology, in which a slider needle/closing wire system penetrates the fleece and typically draws one or two sewing threads laid into it through the fleece during the reverse movement, is particularly suitable. Basically, however, any other stitch-bonding method, such as the Raschel method, for example, can be used to warp-knit the polymer threads 16 in. In this connection, the number of warp threads usually amounts to 3 to 25 per 2.54 cm, preferably about 20 per 2.54 cm. By such a spacing of the warp threads, a sufficient number of loops for hook engagement with a hook tape is formed. The mesh count is preferably 2 to 4 per cm.

Printing of nonwoven textile materials is known and is unproblematic in the case of cellulose substrates. Printing of nonwoven made of polyamide fibers, polyester fibers, and particularly polyolefin fibers is more difficult. Printing inks and pigments that are conventionally used demonstrate only limited adhesion to fiber-type polyolefin structures, and this has a disadvantageous effect on the smear resistance and wear resistance of a printed image. In the case of a laminate according to the invention, a lower smear resistance and wear resistance can be accepted, because the textile cover layer 14 on the top, which has free loops produced by warp knitting, for engagement of hook elements, and itself is not printed, protects the printed image. The printed image is disposed on the side that faces the cover layer 14, and is protected on the underside by the nonwoven and on the top by the textile cover layer 14.

In order to improve the printability and the quality of the printed image, the surface of the nonwoven to be printed can be pretreated. In addition, in the rotary printing method, the printing ink is supposed to be prevented from passing through the nonwoven, since otherwise, the rollers of the printing machine can become contaminated. Aside from the fact that such contamination requires complicated cleaning, residues of ink that dry on can also contribute to fiber break-down or even destruction of the nonwoven, so that a pretreatment on the surface of the nonwoven to be printed is practical, particularly also in order to prevent the printing ink from passing through it. Finally, a laminate glue used when connecting the nonwoven with the cover layer 14 is also supposed to be prevented from passing through. There are various possibilities for a pretreatment. A first embodiment provides for pretreatment of the surface of the nonwoven with a thixotropic primer forming the coating 22. The primer coating 22 fixes the printing ink and contains inorganic fillers, for example a silicon dioxide, titanium dioxide, calcium carbonate, calcined clay, or the like in a suitable binder, in order to improve the absorption and adhesion of the printing ink. The primer, which is adjusted to be thixotropic, acts like a liquid under shear stress and can be applied to the fiber surface of the nonwoven as a thin film, because of its thixotropic properties. Without shear stress, the primer has the properties of a solid that adheres to the fiber surface. The thixotropic properties facilitate application of the primer. For the primer, the binders that are usual for printing inks, such as, for example, nitrocellulose (NC), polyvinyl butyrol (PVB), or polyvinyl chloride (PVC) can be used. It is understood that the primer can also contain resins that crosslink with a reaction agent that hardens at low temperatures as binders. The binder can be applied in an amount between 0.1 $g/m^2$ and 20 $g/m^2$, preferably between 0.5 $g/m^2$ and 2 $g/m^2$.

According to another embodiment of the invention, the surface of the nonwoven to be printed has the coating 22 applied by spraying, which forms an essentially closed skin and preferably has a layer thickness of less than 5 µm. A high-quality printed image can be produced on the closed surface of the sprayed-on layer, since the layer prevents the printing ink from passing through.

Furthermore, a fine-pored coating 22 for absorption of the printing ink can be applied to the surface of the nonwoven to be printed. Fine-pored coatings are known as so-called "foam coatings" and are used for finishing cotton textiles, for example. The pretreatment of the nonwoven layers with a fine-pored coating 22, according to the invention, improves the printability of the nonwoven layers, particularly if these consist of polyolefin fibers. A better print image 18 can be produced on nonwoven layers pretreated in this way, where at the same time, the wear resistance and smear resistance is improved.

Within the scope of the invention, the surface of the nonwoven to be printed is provided with a coating 22 applied by a broad-slit extrusion die, for preparation. In the case of such a so-called curtain coating method, the nonwoven passes through a melt curtain that exits from the broad-slit die.

In addition or as an alternative to the possibilities of pretreatment described, the nonwoven is preferably pretreated by a corona discharge on its printed side. By such a treatment, the surface of the fibers of the nonwoven can be modified in such a manner that they can more easily be printed or provided with an additional coating. The nonwoven can also be pretreated using a plasma process, particularly a plasma coating process. Plasma polymerization processes, in which the surface is modified by deposition of specific materials from the plasma, are particularly suitable. For reasons of process technology, plasma methods that can be carried out at atmospheric pressure are preferably used, because then a complicated vacuum arrangement through which the nonwoven is guided is not required.

Within the scope of the invention, the cover layer 14 and the substrate layer 10 that consists of nonwoven can be glued to one another over their full area or also in sections, for example in a pattern as shown in FIG. 2.

Another aspect of the invention relates to gluing of the cover layer 14 to the substrate layer 10 in a laminate of the type indicated, which is characterized in that the substrate layer 10 consists of nonwoven. In this connection, it is provided that the adhesive is applied to the substrate layer 10 in a pattern, where the pattern has an adhesive frame with adhesive applied over the full area, and, within the adhesive frame, an adhesive structure of regularly disposed adhesive areas and regions that are free of adhesive, and where the adhesive frame forms the edge of the laminate. The gluing process, i.e. the lamination can take place with a reactive PUR adhesive or a hot-melt glue. Since both the substrate layer 10 and the cover layer 14 are formed from textile material, the laminate demonstrates good air permeability. Because gluing occurs only in partial areas, hooking of the laminate into hook-and-loop hooks is facilitated, since the elements that form the male part of a hook-and-loop fastener can engage deeply into the cover layer 14. Full-area gluing of the edge region of the laminate according to the invention prevents the cover layer 14 from being torn out or torn off the substrate layer 10 at the edge when subjected to tensile stress, for example when opening a hook-and-loop fastener formed by the laminate. In particular, a hook-and-loop fastener formed using the laminate can be mused multiple times, without any impairment of function. Furthermore, the hooks can hook less intensively into the glued edge regions of the laminate, thereby causing the material to be subjected to less stress locally when the fastener is opened.

The adhesive areas preferably form a structure in the form of stripes, a lattice, dots, or cells within the adhesive frame, where it is practical if the proportion of adhesive areas within the adhesive frame amounts to between 10% and 70%, preferably between 40% and 60% with reference to the area enclosed by the frame. The proportion of the glued area and the type and form of the adhesive application are determined by the typical opening forces when using the laminate in combination with a suitable hook-and-loop tape.

In order to allow register-precise cutting and application of the individual laminates, in the case of the embodiment described, register marks can be printed onto the laminate. In this connection, the register marks can be visibly printed into the decorative motif. Likewise, an invisible register mark can be provided, which is printed with an ink that is only visible under UV light, for example. Basically, however, the decorative printed indicia 18 can also be detected and used for register-precise handling of the laminates.

We claim:

1. A loop element for a hook-and-loop fastener, the loop element comprising:
 a substrate layer of a nonwoven having an outer face;
 indicia on the outer face of the substrate layer;
 a fleece cover layer on the outer face of the substrate layer;
 an adhesive layer on the outer face securing the cover layer to the substrate layer; and
 a multiplicity of loops formed of polymer threads worked into only the fleece cover layer and projecting from an outer face thereof.

2. The loop element defined in claim 1 wherein the fleece of the cover layer is made of uncrimped endless filaments.

3. The loop element defined in claim 1 wherein the nonwoven of the substrate layer is spun-bonded.

4. The loop element defined in claim 1 wherein the nonwoven of the substrate layer has a surface weight of 10 g/m² to 30 g/m².

5. The loop element defined in claim 1 further comprising a coating of thixotropic primer between the outer face and the indicia.

6. The loop element defined in claim 1, further comprising a coating between the outer layer and the indicia.

7. The loop element defined in claim 6 wherein the coating forms on the outer face a closed skin of a thickness of at least 5 µm.

8. The loop element defined in claim 1, further comprising a coating applied by a slot nozzle to the outer surface of the substrate layer, the indicia being printed on the coating.

9. The loop element defined in claim 1, further comprising a fine-pore coating on the outer surface, the indicia being printed on the coating.

10. The loop element defined in claim 1 wherein the outer face of the substrate layer is treated with a corona discharge or plasma process.

11. The loop element defined in claim 1 wherein the substrate layer and cover layer are adhered together by the adhesive layer over their entire contacting surfaces.

12. The loop element defined in claim 1 wherein the adhesive layer extends between the cover and substrate layers as a continuous frame along edges of the cover and substrate layers and as a plurality of spaced adhesive zones within the frame separated by adhesive-free zones.

13. The loop element defined in claim 12 wherein a ratio of area between adhesive zones and the area enclosed by the frame is 10 to 70%.

14. A loop element for a hook-and-loop fastener, the loop element comprising:
    a substrate layer of a nonwoven having an outer face and formed of a plurality of strata of nonwoven, the stratum forming an inner face opposite the respective outer face being a spunbond;
    a fleece cover layer on the outer face of the substrate layer;
    an adhesive layer on the outer face securing the cover layer to the substrate layer; and
    a multiplicity of loops formed of polymer threads worked into only the fleece cover layer and projecting from an outer face thereof.

15. A loop element for a hook-and-loop fastener, the loop element comprising:
    a substrate layer of a nonwoven having an outer face;
    a fleece cover layer on the outer face of the substrate layer;
    an adhesive layer extending on the outer face between the cover and substrate layers as a continuous frame along edges of the cover and substrate layer and as a plurality of spaced adhesive strips, points, or dots within the frame separated by adhesive-free zones, the frame and the strips, points or dots securing the cover layer to the substrate layer; and
    a multiplicity of loops formed of polymer threads worked into only the fleece cover layer and projecting from an outer face thereof.

16. A loop element for a hook-and-loop fastener, the loop element comprising:
    a substrate layer of a nonwoven having an outer face;
    a fleece cover layer on the outer face of the substrate layer and formed by two bonded-together fleeces of different filaments or fibers;
    an adhesive layer on the outer face securing the cover layer to the substrate layer; and
    a multiplicity of loops formed of polymer threads worked into only the fleece cover layer and projecting from an outer face thereof.

17. The loop element defined in claim 16, further comprising
    indicia on the outer face of the substrate layer.

18. A loop element for a hook-and-loop fastener, the loop element comprising:
    a substrate layer of a nonwoven having an outer face;
    a fleece cover layer on the outer face of the substrate layer;
    an adhesive layer extending on the outer face between the cover and substrate layers as a continuous frame along edges of the cover and substrate layer and as a plurality of spaced adhesive zones within the frame separated by adhesive-free zones, the frame and the adhesive zones securing the cover layer to the substrate layer; and
    a multiplicity of loops formed of polymer threads worked into only the fleece cover layer and projecting from an outer face thereof, a ratio of area between the adhesive zones and the adhesive-free zones being 40 to 60%.

* * * * *